US010702158B2

United States Patent
Varghese et al.

(10) Patent No.: US 10,702,158 B2
(45) Date of Patent: Jul. 7, 2020

(54) LIGHT-BASED COLLAGEN MEASUREMENT SYSTEM AND A SKIN TREATMENT SYSTEM

(71) Applicant: KONINKLIJKE PHILIPS N.V., Eindhoven (NL)

(72) Inventors: Babu Varghese, Eindhoven (NL); Jonathan Alambra Palero, Eindhoven (NL); Martin Jurna, Eindhoven (NL); Margaret Ruth Horton, Eindhoven (NL); Rieko Verhagen, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 229 days.

(21) Appl. No.: 15/510,263
(22) PCT Filed: Aug. 28, 2015
(86) PCT No.: PCT/EP2015/069712
§ 371 (c)(1),
(2) Date: Mar. 10, 2017
(87) PCT Pub. No.: WO2016/041765
PCT Pub. Date: Mar. 24, 2016

(65) Prior Publication Data
US 2017/0251923 A1 Sep. 7, 2017

(30) Foreign Application Priority Data
Sep. 16, 2014 (EP) .................................. 14185025

(51) Int. Cl.
*A61B 5/00* (2006.01)
(52) U.S. Cl.
CPC ............ *A61B 5/0059* (2013.01); *A61B 5/443* (2013.01); *A61B 5/7225* (2013.01); *A61B 5/44* (2013.01); *A61B 2503/12* (2013.01)
(58) Field of Classification Search
CPC ......... A61B 5/0059; A61B 5/44; A61B 5/443; A61B 5/442; A61B 5/444; A61B 5/445; A45D 2044/007
See application file for complete search history.

(56) References Cited

U.S. PATENT DOCUMENTS

2001/0056237 A1  12/2001  Cane
2006/0149343 A1   7/2006  Altshuler
(Continued)

FOREIGN PATENT DOCUMENTS

WO    9528135 A1    10/1995
WO    02094116      11/2002
(Continued)

OTHER PUBLICATIONS

"Quantitative measurements of linear birefringence during heating of native collagen", Lasers in Surgery and Medicine, vol. 20, Issue 3, 1997, pp. 310-318, Duncan J. Maitland and Joseph T. Walsh Jr.
(Continued)

*Primary Examiner* — Christine H Matthews

(57) ABSTRACT

A measurement system is disclosed for light-based measurement of collagen, using a first light intensity and a second light intensity. The measurement system comprises a light source for emitting a light beam having a source wavelength range and an optical system to polarize light within the source wavelength range, thereby generating a polarized light beam, and to direct and focus the polarized light beam to a target position inside the skin at a predetermined focus depth below an outer surface of the skin. The measurement system further comprises a first detector, and a second detector for detecting the first light intensity and the second light intensity within, respectively, a first detection wavelength range and a second detection wavelength range of light reflected from the target position. The measurement system further comprises a comparator, coupled to the first detector and the second detector and configured and arranged to determine a difference between the first light intensity and the second light intensity. When natural collagen is present at the target position, a reflected spectrum of light of the polarized light beam reflected by said natural collagen comprises a plurality of adjacent first and second
(Continued)

wavelength ranges, wherein in said first wavelength ranges constructive interference prevails between the polarized light beam and the natural collagen, and wherein in said second wavelength ranges destructive interference prevails between the polarized light beam and the natural collagen.

21 Claims, 2 Drawing Sheets

(56) References Cited

U.S. PATENT DOCUMENTS

2008/0194928 A1  8/2008  Bandic
2012/0296238 A1  11/2012 Chernov

FOREIGN PATENT DOCUMENTS

| WO | 2009089292 A1 | 7/2009 |
| WO | 2009105250 A2 | 8/2009 |
| WO | 2011112248 A2 | 9/2011 |
| WO | 2013128330 A1 | 9/2013 |

OTHER PUBLICATIONS

"Skin responses to fractional photothermolysis", Laubach, Tannous et al, Lasers Surg. Med., 38: 142-149 (2006).
"Imaging thermally damaged tissue by polarization sensitive optical coherence tomography", Johannes F. de Boer, Shyam M. Srinivas, Arash Malekafzali, Zhongping Chen and J. Stuart Nelson, Sep. 14, 1998, vol. 3, No. 6, Optics Express, 212-218.
"Collagen denaturation can be quantified in burned human skin using polarization-sensitive optical coherence tomography", Pierce, Sheridan et al, Burns, 30(6), (2004).

LIGHT-BASED COLLAGEN MEASUREMENT SYSTEM AND A SKIN TREATMENT SYSTEM

This application is the U.S. National Phase application under 35 U.S.C. § 371 of International Application No. PCT/EP2015/069712, filed on Aug. 28, 2015, which claims the benefit of International Application No. 14185025.5 filed on Sep. 16, 2014. These applications are hereby incorporated by reference herein.

FIELD OF THE INVENTION

The invention relates to a measurement system for light-based measurement of collagen inside skin.

The invention further relates to a skin treatment system comprising the measurement system according to the invention.

BACKGROUND OF THE INVENTION

The desire to maintain a youthful appearance by reducing wrinkles in the skin is an important issue in human society. Many techniques have been designed to achieve this goal. One of the techniques is, for example, skin rejuvenation, particularly methods that involve denaturation of collagen, such as thermal denaturation of collagen. Although some therapeutic applications are possible, the main area of interest is in the cosmetic, or non-therapeutic, field. The efficacy of such methods in the skin depends on several factors, such as thermal and mechanical load on the tissue, age of the person undergoing the treatment, anatomical distribution of collagen inside the skin, diseases of the skin, environmental exposure, skin type, etc. At present the parameters of the denaturation-based skin rejuvenation treatments are often based on trial and error.

An increasing number of these skin treatments and skin treatment systems are intended for use by consumers rather than medical professionals. These treatment systems are non-invasive—they create an effect beneath the surface of the skin without having to physically penetrate the epidermis. However, such home-use systems raise new concerns, such as concerns relating to safety and treatment efficacy. This is particularly important when the light source for performing the treatment is a laser, and incorrect operation of such a laser can result in scarring or burning of the skin at locations where the laser light passes through the skin layers.

Damage to the epidermis, for example, is highly undesirable because this may lead to complications and health risks to the person being treated, as well as social downtime. If superficial lesions are created above the dermis, petechiae (micro-bleeding) may occur due to micro-rupturing of capillaries, resulting in reduced efficacy and an increase in side effects. The formation of new collagen for the purpose of skin rejuvenation will occur if the collagen is denaturized. The efficacy of a thermal treatment for collagen denaturation, and the subsequent collagen remodeling, are high only if the temperature inside the dermis exceeds a critical temperature of 65 degrees C. Treatments are therefore provided which direct considerable amounts of energy to raise the temperature of the skin above the threshold required for denaturation.

Treatment of skin regions where no collagen is present may result in over-treatment. Assuming collagen is present, changes in the length of the collagen fibers continue during denaturation until the fibers have shrunk to a minimum length—thermal treatment beyond this phase is over-treatment because the collagen structure is completely disrupted. Over-treatment may result in unnecessary damage to surrounding tissues and other side effects without promoting any rejuvenation and tightening effect.

Because the effectiveness and safety of denaturation of collagen and the resulting skin rejuvenation depend on several factors (as indicated hereinbefore), there is a need to measure the presence of collagen, and to measure the denaturation of collagen inside the skin during the course of treatment.

It is known to use the birefringence of collagen to determine the presence of collagen by tracking the changes seen in the reflected light when the skin is subjected to polarized light, and to repeat such measurements to monitor the progression of the denaturation. This is one of the measurement systems described in WO 2011/112248. Such monitoring systems may be used in combination with many different treatment methods, such as R.F. (radio frequency)-based, U.S. (ultra-sound)-based or laser-based treatment methods. Drawbacks of such known measurement methods reside in that they are relatively complex and time consuming. For example, optical measurement is described in detail in "Quantitative measurements of linear birefringence during heating of native collagen", Lasers in Surgery and Medicine, Vol. 20, Issue 3, 1997, Pages: 310-318, Duncan J. Maitland and Joseph T. Walsh Jr. The birefringence is measured at a number of points in time by deriving a mean and standard deviation from 60 measurements, using a compensation crystal and a polarizing transmission microscope.

WO 1995/28135 describes a further technique in which the gradual change in intensity and the color change observed when using a polarizing transmission microscope are dealt with. However, the perception of color change and intensity change may differ between different observers, which makes the values subjective. The measurement is not an accurate and quantitative measure of the progression of the treatment, since color change and diminution due to the collagen depend on many factors, including age, skin-optical and thermal properties etc.

OBJECT OF THE INVENTION

It is an object of the invention to provide a measurement system for light-based measurement of collagen inside skin, which is less complex and which provides a less subjective measurement result.

SUMMARY OF THE INVENTION

A first aspect of the invention provides a measurement system for light-based measurement of collagen inside skin, using a first light intensity and a second light intensity. A second aspect of the invention provides a skin treatment system.

The measurement system according to the invention comprises an optical system having a light source configured and arranged to emit a light beam having a source wavelength range, the optical system being configured and arranged:

to polarize light within the source wavelength range, thereby generating a polarized light beam; and to direct and focus the polarized light beam to a target position inside the skin at a predetermined focus depth below an outer surface of the skin;

the measurement system further comprising:

a first detector configured and arranged to detect the first light intensity within a first detection wavelength range of light reflected from the target position;

a second detector configured and arranged to detect the second light intensity within a second detection wavelength range of light reflected from the target position, and a comparator, coupled to the first detector and the second detector and configured and arranged to determine a difference between the first light intensity and the second light intensity;

wherein, with reference to a reflected spectrum of light of the polarized light beam reflected by natural collagen when present at the target position, said reflected spectrum comprising a plurality of adjacent first and second wavelength regions, wherein in said first wavelength regions constructive interference prevails between the polarized light beam and the natural collagen, and wherein in said second wavelength regions destructive interference prevails between the polarized light beam and the natural collagen:

the first detection wavelength range is predetermined and/or controlled to be confined to one or more of said first wavelength regions; and the second detection wavelength range is predetermined and/or controlled to be confined to one or more of said second wavelength regions.

The spectrum of the polarized light reflected by natural collagen comprises a plurality of adjacent first and second wavelength regions, wherein in said first wavelength regions constructive interference prevails between the polarized light beam and the natural collagen, and wherein in said second wavelength regions destructive interference prevails between the polarized light beam and the natural collagen. This is caused by the birefringence properties of natural collagen and may be referred to as spectral modulation of the polarized incident light due to the presence of natural collagen at the target position. In said second wavelength regions where destructive interference between the polarized incident light and the natural collagen occurs or prevails, a dark band is observed in the reflected wavelength spectrum due to the light waves being exactly 180 degrees out of phase. In said first wavelength regions where constructive interference between the polarized incident light and the natural collagen occurs or prevails, a bright band is observed in the reflected wavelength spectrum due to the light waves being in phase.

The invention is based on the insight that, for a chosen focusing depth in the skin, the wavelengths at which the bright bands caused by said constructive interference occur in the reflected wavelength spectrum are relatively constant. The first detection wavelength range of the light reflected from the target position is confined to one or more of these wavelengths of the bright bands. Similarly, for a chosen focusing depth in the skin, also the wavelengths at which the dark bands caused by said destructive interference occur in the reflected wavelength spectrum are relatively constant. The second detection wavelength range of the light reflected from the target position is confined to one or more of these wavelengths of the dark bands.

In other words, the invention provides a measurement system which enables collagen detection at a chosen focusing depth and which operates satisfactorily when treating different subjects or different areas of the body. By measuring the light intensity within a wavelength band where constructive interference between the incident light and the collagen occurs or prevails, and by comparing this light intensity with a light intensity measurement within a wavelength band where destructive interference between the incident light and the collagen occurs or prevails, the presence of collagen may be determined. If no collagen is present in the target position, or the collagen that was present has denatured sufficiently below a critical detection point, the first light intensity and the second light intensity of the reflected light will be substantially identical. If natural collagen is present in the target position, either because it has not yet been treated (i.e. denatured) or it has been treated (i.e. denatured) only partially, the first light intensity and the second light intensity of the reflected light will be substantially different, i.e. the first light intensity will be substantially higher than the second light intensity.

It may be advantageous to predetermine and/or control the first detection wavelength range to be confined to one or more of said plurality of first wavelength regions wherein constructive interference of second order or higher order prevails between the polarized light beam and the natural collagen, and to predetermine and/or control the second detection wavelength range so as to be confined to one or more of said plurality of second wavelength regions wherein destructive interference of second order or higher order prevails between the polarized light beam and the natural collagen.

When using wavelength ranges wherein, instead of first-order interference, second-order or higher-order interference occurs or prevails, the separation between the central wavelengths of the first detection wavelength range and the second detection wavelength range will decrease substantially. This will reduce any intensity variations in the reflected light caused by a relatively large separation of the detection wavelength ranges. If the two detection wavelength ranges corresponding to the occurrence of constructive and destructive interference are sufficiently close to each other, the influence of wavelength-dependent scattering effects will be reduced. In some cases, the influence may even become negligible.

For widely spaced detection wavelength ranges, the amount of backscattered light depends, inter alia, on the wavelength before and after the treatment. This may negatively influence the measurement result, and may partially or wholly mask the wavelength-dependent birefringence effect measured by the measurement system.

The optical system may be further configured and arranged to focus the polarized light beam at a target position between 100 micron and 1000 micron below the outer surface of the skin. Within this range of focus depths, the spectral modulation due to the birefringence of the natural collagen will be substantially constant. In other words, the first and second detection wavelength ranges may be predetermined and/or controlled to perform collagen measurement at the selected focus depth at different positions on the body, and even on different subjects, without any significant recalibration. The measurement system according to the invention may be greatly simplified, because the first and second detection wavelength ranges may be considered fixed, although in practice some degree of recalibration may be required due to other aspects, such as spectral sensitivity of the detectors, and emission spectrum of the light source.

At a chosen focus depth, the second detection wavelength range may further be predetermined and/or controlled to extend over a band of less than 100 nm, preferably less than 50 nm, more preferably less than 30 nm, even more preferably less than 20 nm. In such an embodiment, suitable detectors may be applied comprising an intensity detector and an appropriately dimensioned bandpass filter. In practice, these detection wavelength ranges may operate satisfactorily when the variations in the chosen focus depth are 50 microns or less.

At a chosen focus depth, a difference between a central wavelength of the first detection wavelength range and a central wavelength of the second detection wavelength range may be less than 300 nm, preferably less than 100 nm, more preferably less than 50 nm, even more preferably less than 30 nm. When measuring is performed at lower orders of interference, the central wavelengths of the detection wavelength ranges may typically have a separation of between 300 and 400 nm. At higher orders of interference and at small focus depths, the separation between the central wavelengths of the detection wavelength ranges may be substantially smaller.

In a preferred embodiment of the measurement system according to the invention, the first detection wavelength range is predetermined and/or controlled to be confined to a single one of said plurality of first wavelength regions, and the second detection wavelength range is predetermined and/or controlled to be confined to a single one of said plurality of second wavelengths regions, wherein said single one of said plurality of first wavelength regions is adjacent to said single one of said plurality of second wavelength regions. In this preferred embodiment, the first detector of the measurement system may comprise a single photodiode to measure the first light intensity, and the second detector of the measurement system may comprise a single photodiode to measure the second light intensity. By utilizing only two photodiodes for detection, a compact and cheap measurement system is provided.

The measurement system may be further configured and arranged such that the first detector comprises:

at least two detector channels, each detector channel being configured and arranged to detect a light intensity within a different one of said plurality of first wavelength regions; and a processor, coupled to each detector channel and configured and arranged to determine the first light intensity from the light intensities detected by said at least two detector channels.

It may be advantageous to perform measurements in a plurality of bright wavelength bands to improve the accuracy and reliability of the measurement. This may be done in combination with a measurement in a single dark wavelength band or in a plurality of dark wavelength bands.

Similarly, it may be advantageous for the measurement system to be further configured and arranged such that the second detector comprises:

at least two detector channels, each detector channel being configured and arranged to detect a light intensity within a different one of said plurality of second wavelength regions; and a processor, coupled to each detector channel and configured and arranged to determine the second light intensity from the light intensities detected by said at least two detector channels.

It may be advantageous to perform measurements in a plurality of dark wavelength bands to improve the accuracy and reliability of the measurement. This may be done in combination with a measurement in a single bright wavelength band or in a plurality of bright wavelength bands.

The skin treatment system according to a further aspect of the invention comprises the measurement system according to the invention.

Denaturation of collagen may, for example, be done using a focused treatment energy source, for example, a radiofrequency (RF) energy source or an ultrasound energy source or, for example, a light or laser source providing treatment light. The measurement system may, for example, measure the denaturation process in real-time during the operation of the RF energy source or the laser source providing the treatment. During the treatment, the length of the collagen fibers changes until the fibers have shrunk to a critical length, and denaturation treatment beyond this phase seems not effective anymore for further skin treatment, e.g. skin rejuvenation, because the collagen structure is completely disrupted at this treatment location. The difference between the first light intensity and the second light intensity measured by the measurement system during the treatment will gradually decrease and may, for example, stabilize at a substantially zero difference, which indicates that further treatment seems not effective and preferably should be discontinued to avoid adverse side effects such as skin damage.

These and other aspects of the invention are apparent from and will be elucidated with reference to the embodiments described hereinafter.

DETAILED DESCRIPTION OF EMBODIMENTS

Figure 1:
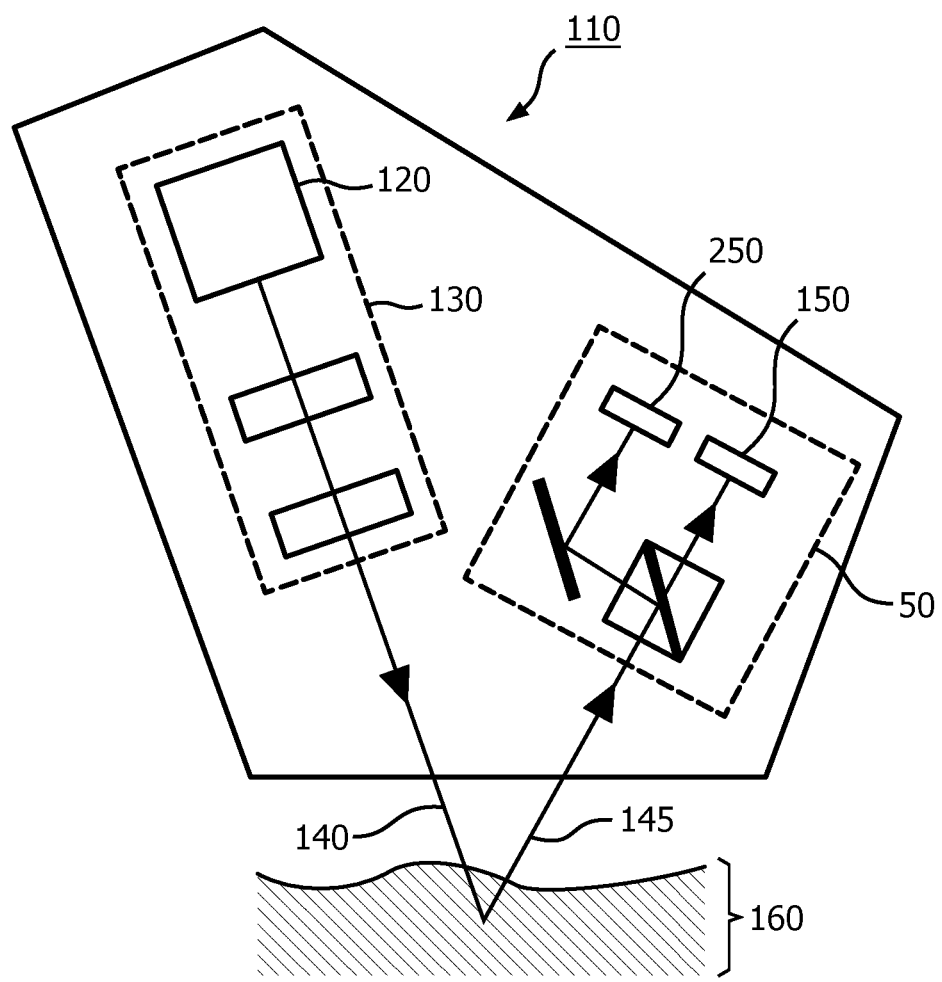
FIG. 1 schematically shows a measurement system according to the invention.

FIG. 1 schematically shows a skin measurement system 110 according to the invention. The measurement system 110 is configured and arranged for light-based measurement of collagen inside the skin 160. The measurement system 110 comprises an optical system 130, which comprises a light source 120 for emitting light over a predetermined and/or controlled source wavelength range.

The light source 120 is preferably a polychromatic source which emits a relatively broad spectrum of wavelengths. In other words, it should not be monochromatic. Or in still other words, it should be polychromatic or broadband or "white". The skilled person may use techniques known in the art to determine the optimum source wavelength range, or bandwidth, using a plurality of light sources simultaneously, or a broadband light source in combination with one or more suitable bandpass filters.

Examples of a polychromatic or broadband light source are:

tungsten lamps having an emission spectrum in the range of 300-1000 nm;

a Superluminiscent Laser Diode (SLD), which typically emits light over a range ($\Delta\lambda$) of 10-100 nm or a Light-Emitting Diode (LED) which typically emits light over a range (($\Delta\lambda$) of 50-200 nm.

Alternatively, the polychromatic or broadband source may comprise two or more monochromatic (or narrowband) sources, operated simultaneously. For example, a first and second monochromatic light source may be used, each having spectral emission in the range of 200-500 nm and a spectral bandwidth of 10-50 nm. More preferably, each monochromatic light source may have spectral emission in the range of 300-400 nm and a spectral bandwidth of 10-20 nm.

The optical system 130 further comprises optical elements such that the light beam from the light source 120 is polarized over substantially the entire source wavelength range, thereby generating a polarized light beam 140, and such that the polarized light beam 140 is directed and focused to a target position inside the skin 160 at a predetermined focus depth below the outer surface of the skin. The skilled person may select any combination of light source and optical element known in the art to achieve this. For example, a non-polarized light source 130 may be provided in combination with a polarizing element, or a polarized light source 130 may be provided. Similarly, a combination of polarizing elements may be provided, wherein one or more of said polarizing elements are comprised in the light source 120 and one or more polarizing elements 130 are comprised in the optical system 130.

In another example, a transmissive polarizing element may be placed such that it intersects the light beam between the light source 120 and the target position inside the skin 160. The measurement system 110 will provide incident light in the target position with the same polarization direction or orientation for a broad spectrum of light wavelengths. For example, a wire grid polarizer may be used.

As the skilled person will be aware, the polarized light beam at the target area may be provided by using a reflective polarizing element 130, such as an LCOS (Liquid Crystal On Silicon) element. In some embodiments, a combination of transmissive and reflective optical elements in the optical system 130 may also be advantageous.

The optical system 130 provides a polarized light beam 140, which preferably is linearly polarized.

The polarized light beam 140 is incident on an outer layer of skin during use. The optical system 130 is predetermined and/or controlled such that the direction (or orientation) of the polarization is substantially the same throughout substantially the entire source wavelength range.

The measurement system 110 is configured and arranged such that the light emitted may penetrate through the outer layer of skin to reach the target position inside the skin at a predetermined focus depth below the outer surface of skin. The focus depth is chosen to correspond to a depth at which collagen is expected to be found.

The measurement system 110 further comprises a detection unit 50 comprising a first detector 150 and a second detector 250. The detection unit 50 is further configured to direct light reflected 145 from the target position in the skin 160 to both the first detector 150 and the second detector 250. The detection unit 50 further comprises one or more optical members known in the art to achieve this result, such as the 50/50 beam splitter and folding mirror, which is depicted in FIG. 1. As the collagen measurement is related to the light-intensity difference measured by and between the first detector 150 and the second detector 250, it may be advantageous to configure the beam paths to the detectors to be as equal as possible.

The first detector 150 is configured and arranged to detect a first light intensity within a first detection wavelength range of light 145 reflected from the target position. The second detector 250 is configured and arranged to detect a second light intensity within a second detection wavelength range of light 145 reflected from the target position. For this purpose, for example, each detector 150, 250 may be preceded by a suitably dimensioned bandpass filter.

A comparator, not shown in FIG. 1, is coupled to both the first detector 150 and the second detector 250 and is configured and arranged to determine a difference between the first light intensity and the second light intensity.

The measurement system 110 is configured to measure collagen at a predetermined focus depth in the skin. This includes predetermining and/or controlling the first detection wavelength range and the second detection wavelength range. These wavelength ranges may be predetermined experimentally by measurements on a wide range of subjects and skin regions, or by computer simulation for a chosen focus depth. The detection wavelength ranges depend inter alia on the birefringence properties of the collagen, which are well known, and on the optical path length, which depends on the focus depth below the outer surface of the skin.

For example, based on simulation data at a source wavelength range of 300-1000 nm, the following wavelength ranges may be used. In this example, the second detection wavelength range extends between the expected boundaries of the dark band within the reflected spectrum, and the first detection wavelength range corresponds to the wavelength region with the highest intensity (bright band) between two adjacent dark bands.

1. Focus depth: 250 microns±50 microns
A. First-order interference wavelength bands
First (bright) detection wavelength range: 1000-1100 nm
Second (dark) detection wavelength range: 660-740 nm
Bandpass filter for the first detector: 1050 nm±50 nm
Bandpass filter for the second detector: 700 nm±40 nm
Separation between the detection ranges: 350 nm
B. Second-order interference wavelength bands
First (bright) detection wavelength range: 500-550 nm
Second (dark) detection wavelength range: 400-440 nm
Bandpass filter for the first detector: 525 nm±25 nm
Bandpass filter for the second detector: 420 nm±20 nm
Separation between the detection ranges: 105 nm
C. Third-order interference wavelength bands
First (bright) detection wavelength range: 280-310 nm
Second (dark) detection wavelength range: 330-360 nm
Bandpass filter for the first detector: 295 nm±15 nm
Bandpass filter for the second detector: 345 nm±15 nm
Separation between the detection ranges: 50 nm
D. Fourth-order interference wavelength bands
First (bright) detection wavelength range: 220-240 nm
Second (dark) detection wavelength range: 250-275 nm
Bandpass filter for the first detector: 230 nm±10 nm
Bandpass filter for the second detector: 262.5 nm±12.5 nm
Separation between the detection ranges: 32.5 nm
2. Focus depth: 500 microns±50 microns
A. First-order interference wavelength bands
First (bright) detection wavelength range: 1000-1100 nm
Second (dark) detection wavelength range: 800-880 nm
Bandpass filter for the first detector: 1050 nm±50 nm
Bandpass filter for the second detector: 840 nm±40 nm
Separation between the detection ranges: 210 nm
B. Second-order interference wavelength bands
First (bright) detection wavelength range: 670-730 nm
Second (dark) detection wavelength range: 570-630 nm
Bandpass filter for the first detector: 700 nm±30 nm
Bandpass filter for the second detector: 600 nm±30 nm
Separation between the detection ranges: 100 nm
C. Third-order interference wavelength bands
First (bright) detection wavelength range: 510-540 nm
Second (dark) detection wavelength range: 450-480 nm
Bandpass filter for the first detector: 525 nm±15 nm
Bandpass filter for the second detector: 465 nm±15 nm
Separation between the detection ranges: 60 nm Although wavelength regions, wherein any order of interference occurs, may be used, the wavelength regions, wherein higher order interference occurs, are preferred, because the smaller separation between the detection wavelength ranges, occurring for the higher order interference wavelength regions, is expected to reduce the wavelength-dependent scattering influencing the light-intensity values measured. The skilled person may use trial and error experiments to determine the most appropriate wavelength ranges.

It may be also advantageous for the measurement system 110 to further comprise a processor, connected to the comparator, and configured to determine a degree of collagen denaturation, based on the difference between the measured first light intensity and second light intensity. Although the detection of a distinct difference may give a suitable signal indicating the presence, or not, of collagen, a more complex system in which each difference measurement is compared to earlier difference measurements may be used to determine the degree of denaturation and/or the point of denaturation in a course of treatment.

Optionally, the processor may be provided with additional data such as details concerning the person or body region being treated, or the treatment. Examples of additional data include: age, skin color, stage in the treatment, position of the target positions and intensity measurement positions on the body. In the simplest embodiment, this data may be recorded solely for more detailed reporting. Although not essential to the invention, the data may also be used to increase the accuracy of the collagen measurement if the processor is provided with appropriate calculation algorithms or look-up tables.

During use, the polarized light beam 140 is focused at a target position at a predetermined focus depth below the outer surface of the skin, preferably in the range of 100-1000 micron. The detector unit receives the reflected light 145 from the target position, and directs the reflected light through a first bandpass filter to the first detector, which measures the first light intensity, and also directs the reflected light through a second bandpass filter to the second detector, which measures the second light intensity. The comparator determines the difference between the first light intensity and the second light intensity. It is well known that natural collagen is a birefringent tissue constituent, and the birefringence ($\Delta n$) is estimated to be $2.8 \times 10-3-3.0 \times 10-3$. When linearly polarized light interacts with birefringent natural collagen structures, the intensity of reflected light detected depends on the orientation of the incident polarization direction relative to the collagen fibers. In some prior art systems, this may sometimes give an incorrect assessment of the presence of collagen due to an unexpected fluctuation in the light-intensity measurements caused by a body or region absorbing some of the light. In the invention, the target position is illuminated with broadband or polychromatic light, making the measurement more reliable as fluctuations due to absorbent regions or bodies in the skin have a smaller influence on the overall measurement of collagen presence. Such absorbent regions or bodies typically only absorb in a narrow range of wavelengths.

If natural collagen is present at the target position, in the form of untreated collagen or partially treated collagen or collagen in its initial state, the incident broadband polarized light 140 interacts with birefringent collagen structures, which results in an alternating pattern of maxima and minima at certain wavelengths in the measured light intensity of the reflected light, depending, inter alia, on the optical path length difference of the birefringent collagen fibers, the source wavelength range of the incident light, the properties of the birefringent collagen, including the difference between the refractive index and the birefringence of the two beams, which has a maximum value dependent on the specimen and on the direction of travel of light. In other words, the reflected spectrum of light of the polarized light beam 140 reflected by natural collagen in the target position comprises a plurality of adjacent first and second wavelength regions, wherein in said first wavelength regions constructive interference prevails between the polarized light beam and the natural collagen, and wherein in said second wavelength regions destructive interference prevails between the polarized light beam and the natural collagen. The minima in the reflected spectrum may be observed as dark bands at certain frequencies due to the destructive interference.

The second detection wavelength range is predetermined and/or controlled to be confined to a wavelength region wherein destructive interference occurs or prevails. The destructive interference forms dark bands in the reflected spectrum where the detected light intensity is relatively low and may even be approximately zero. The second detection wavelength range comprises at a least a portion of one of the dark bands in the reflected spectrum. Typically, the second detection wavelength range may have boundaries approximately equal to the boundaries of the dark band selected for the measurement, in which case the second detection wavelength range will comprise substantially the whole band. In some cases, the second detection wavelength range may comprise a dark band and a small portion of an adjacent bright band at the periphery of the dark band. In these cases, the extent of the second detection wavelength range should be such that, within the detected second wavelength region, destructive interference prevails, so that, when naterual collagen is present in the target position, the light intensity or average light intensity measured within the second detection wavelength range is smaller than the light intensity measured within the adjacent first detection wavelength range.

The first detection wavelength range is predetermined and/or controlled to be confined to a wavelength region wherein constructive interference occurs or prevails. The first detection wavelength range may substantially avoid the dark bands, in other words it may be confined to a wavelength region between two adjacent dark bands where the measured light intensity is relatively high. The second detection wavelength range comprises at least a portion of one of the bright bands in the reflected spectrum. Preferably, the second detection wavelength range comprises the wavelength region wherein the measured light intensity is at the highest level, i.e. at the brightest level, and preferably it comprises the approximately central part of the wavelength band wherein constructive interference occurs. This provides the largest possible difference between the measured first light intensity and the second light intensity when collagen is present at the target position. In some cases, the first detection wavelength range may comprise a bright band and a small portion of an adjacent dark band at the periphery of the bright band. In these cases, the extent of the first detection wavelength range should be such that, within the detected first wavelength region, constructive interference prevails, so that, when naterual collagen is present in the target position, the light intensity or average light intensity measured within the first detection wavelength range is higher than the light intensity measured within the adjacent second detection wavelength range.

The measurement system provides a relatively simple and stable way of measuring collagen compared to the known methods. The measured difference between the first and second light intensities is related to the amount of untreated or undenatured collagen, so that a quantitative measurement may also be provided. This makes it simpler to integrate the measurement system into a skin treatment device, and repeated measurements may provide more accurate monitoring of the collagen denaturation process as compared to currently available measurement systems.

The detection unit 50 may be any suitable arrangement that can determine an intensity difference in the reflected light between a dark and a bright band.

The first detector 150 and the second detector 250 may be relatively simple photodiodes or any other detector able to detect the intensity of the reflected light, preceded by a suitably selected narrow bandpass filter to select the respective wavelength for detection.

The first detector 150 may comprise two or more detector channels, each detector channel being configured and arranged to detect a light intensity within a different one of the first wavelength regions of the reflected light wherein constructive interference occurs or prevails. In this embodiment the measurement system comprises a processor, coupled to each detector channel and configured and arranged to determine the first light intensity from the light intensities detected by said two or more detector channels.

Alternatively and/or additionally, the second detector 150 may comprise two or more detector channels, each detector channel being configured and arranged to detect a light intensity within a different one of the second wavelength regions of the reflected light wherein destructive interference occurs or prevails. In this embodiment the measurement system comprises a processor, coupled to each detector channel and configured and arranged to determine the second light intensity from the light intensities detected by said two or more detector channels.

By measuring in two or more different wavelength regions of constructive interference and/or two or more different wavelength regions of destructive interference, the reliability of the overall measurement may be improved. Each detector channel may comprise a single photodiode.

The detection unit 50 may similarly be any suitable arrangement known in the art, such as a spectrometer, spectrophotometer, spectrograph, spectroscope or spectral analyzer. In a further example, the detection unit 50 may, for example, comprise an array of detectors, such as a CCD array, preceded by a suitably dimensioned grating to distribute a plurality of wavelengths over a plurality of positions on the CCD array. The CCD array could have dimensions ranging between a few mm's and one or more cm's, and may be provided with a diffraction grating with a pitch of a few tens of microns. The skilled person will be able to use simple trial and error experiments to provide a suitable dispersion and detection of the dark and bright bands in the reflected spectrum. A processor may be configured for comparing areas of the array to determine the difference between the light intensities of the dark and bright bands.

In an embodiment of the measurement system, a central wavelength of the source wavelength range of the light beam emitted by the light source is in a range from visible light to infrared light. The light source may provide polychromatic or broadband light, for example in the range of 300 nm to 1000 nm. A broad range is preferred to increase the reliability of the measurement, so that false minima, such as caused by a chromophore absorbing a particular wavelength, may be avoided. The skilled person may select the source wavelength range based on factors such as available light sources, expected absorption wavelengths of the skin to be measured, and the difficulty of manufacturing a broadband linear polarizer.

The central wavelength of the source wavelength range may be between 300 nanometer and 2000 nanometer. A suitable infrared wavelength, for which relatively high intensity light sources are available, is the 1064 nm wavelength, which is extensively used in glass-fiber communication networks. High intensity photodiodes emitting light of 1064 nanometer are relatively good light sources for use in the measurement system according to the invention, as these photodiodes have a relatively high intensity, are still relatively small and have a relatively good penetration depth of the emitted light into the target position inside the skin. A plurality of such laser diodes may be used simultaneously to provide a polychromatic or broadband source.

Additional optical elements known in the art may also be provided in the optical system 130 to further guide and modify the incident light beam 140 and the reflected light beam 145.

The measurement system 110 may also be configured to exclude certain wavelengths. The range of light wavelengths 140 incident on the skin may be the same as that produced by the light source, or the range may be reduced compared to that of the light source 120 by providing a further, suitably selected, bandpass filter. Alternatively or additionally, a bandpass filter may be placed in the path of the reflective light 145 to further improve the detection.

In practice, it may also be necessary to correct for wavelength-dependent absorption and scattering losses in the skin. This may be done by suitably modifying the measurement system 110 and/or configuring the processor.

The interaction of polarized incident light beam 140 with birefringent collagen fibers depends on the orientation of the polarization direction of the incident polarization light beam 140 relative to the collagen fiber axis, so that it may also be advantageous to provide means to control the polarization direction during use such that the user may determine the optimal configuration.

Figure 2A:
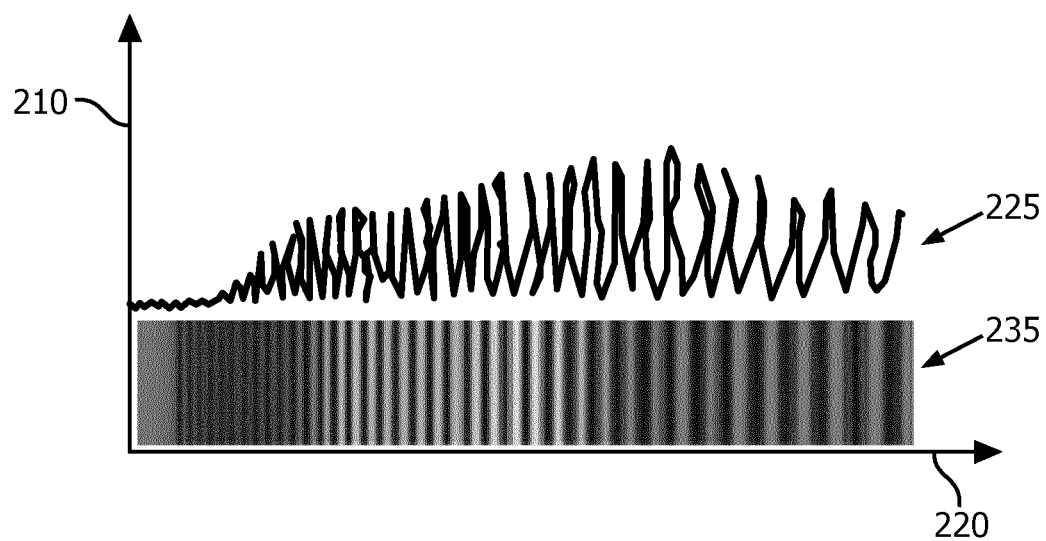
FIG. 2A is a graph showing the variation of the light intensity at a plurality of wavelengths of the light reflected from the target position when natural collagen is present in the target position.
Figure 2B:
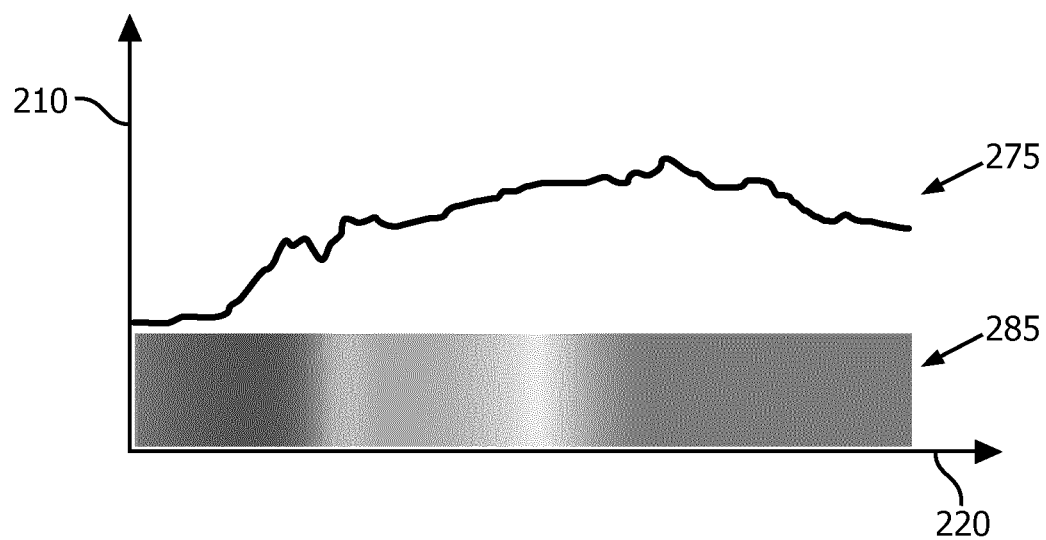
FIG. 2B is a graph showing the variation of the light intensity at a plurality of wavelengths of the light reflected from the target position when no collagen is present in the target position, or when the collagen has denatured or almost completely denatured.

FIGS. 2A and 2B depict graphs of the measured light intensity 225 of the reflected light (along the vertical axis 210) versus the wavelength of the reflected light (along the horizontal axis 220) when natural collagen in present in the target position.

FIG. 2B shows the light intensity measurements 275 after treatment when the collagen in the target position has denatured and is no longer detectable. For the lowest wavelengths of the spectrum, a minimum or zero light intensity level is detected. For higher wavelengths of the spectrum, the reflected light intensity sharply increases. As the wavelength increases further, the reflected light intensity increases slightly to an overall maximum, followed by a gradual decrease for the highest wavelengths of the spectrum. FIG. 2B also depicts, proximate the horizontal axis 220, the visible color spectrum 285 (ranging from violet to red) corresponding to the wavelengths of the horizontal axis 220. The light intensity profile 275 shows no particular minima associated with the presence of natural collagen, and the visible color spectrum 285 shows no dark bands. This light intensity profile 275 could also be described as the reflected spectral response of skin when illuminated with a broadband polarized source having no collagen (or fully denatured collagen) in the target position.

FIG. 2A shows how the intensity measurements 225 and visible spectrum 235 are modified by the presence of natural collagen. In FIG. 2A, the light intensity profile 225 has an upper light intensity level which is approximately the same as the upper light intensity level of the light intensity profile 275 depicted in FIG. 2B. The light intensity profile 225 of FIG. 2A comprises alternating maxima and minima, wherein the maxima reach said upper light intensity level and the minima reach a minimum or zero light intensity level. The light intensity profile 225 is approximately sinusoidal, with the minima being mutually separated. The visible spectrum 235 comprises dark bands at the wavelengths where the intensity minima 225 occur.

In FIG. 2A, before treatment (denaturation) of the collagen, the difference in light intensity between each one of the minima and the immediately adjacent maxima is substantial. For example, the light intensity at each minimum is approximately 0-20% of the light intensity of the immediately adjacent maxima, and in many cases will reach the zero level.

The detection of the amplitude of this approximately sinusoidal pattern provides a method of measuring the birefringence of the collagen fibers. When the collagen is fully denatured (or not present), the intensity profile 275 and the visible spectrum 285 show no minima or dark bands at all. The difference in light intensity between adjacent maxima and minima in the reflected spectrum provides an indication of the degree of denaturation of the collagen.

During thermal denaturation of collagen, the birefringence property of collagen is lost, depending on the increase in temperature. Typically, the collagen is heated from approximately 40 degrees C. to at least 65 degrees C., resulting in a loss of birefringence by a factor of 10. As the collagen denatures, the degree of denaturation may be determined by comparing the current situation with the one at the start of the treatment, or by comparing the current situation with reference values.

Collagen denaturation and collagen fiber shrinkage by thermal treatment is described, for example, in "Skin responses to fractional photothermolysis", Laubach, Tannous et al, Lasers Surg. Med., 38: 142-149 (2006). The polarization dependence of the measurement on collagen shrinkage is disclosed in, for example, "Collagen denaturation can be quantified in burned human skin using polarization-sensitive optical coherence tomography", Pierce, Sheridan et al, Burns, 30(6), (2004).

The measurement system 110 may also be comprised in a skin treatment system comprising a treatment source. Such a treatment source may, for example, be an RF radiation source or, for example, a laser source for providing treatment light, typically a pulsed laser beam. The treatment source may, for example, be a Nd:YAG laser with emission at 1064 nm.

The treatment source beam path may be completely separate or partially integrated into the beam path of the measurement system. For example, if the treatment source is a laser, said laser may also be used as the light source 120. If the treatment beam is an R.F beam, the measurement system 110 will be functionally quite separate from the treatment function. In such an embodiment, the measurement system 110 may be used as feed-back system for measuring efficacy of the denaturation treatment of collagen fibers by the treatment source. In such a case, the comparator may also be connected to the treatment source to control the treatment source, for example, to control the treatment duration or the treatment intensity.

The measurement system 110 may perform real-time measurements continuously during the denaturation treatment, or may perform several measurements during the denaturation treatment which together provide feedback about the denaturation process and the current state of the denaturation treatment.

Additionally or alternatively, the measurement system may be configured and arranged such that the paths of the incident light beam 140 and the reflected light beam 145 partially coincide. This may reduce the dimensions of the measurement system, and it allows both the incident light beam 140 and the reflected light beam 145 to be approximately perpendicular to an outer layer of skin.

Although the invention is particularly suited for collagen measurement, the skilled person will also be able to configure the invention for use in detecting other skin birefringent structures, such as tendons, elastins, hair, and for monitoring the changes in measurement due to the corresponding treatment, such as photoepilation.

It may also be advantageous to configure and arrange the measurement system to determine the presence of a plurality of types of skin birefringent structures.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the system claim enumerating several means, several of these means may be embodied by one and the same item of hardware. The mere fact that certain measures are recited in mutually different dependent claims does not indicate that a combination of these measures cannot be used to advantage.

The invention claimed is:

1. A measurement system for light-based measurement of collagen inside skin, using a first light intensity and a second light intensity, the measurement system comprising:
   an optical system having a light source configured and arranged to emit a light beam having a source wavelength range;
   the optical system being configured and arranged:
   to polarize light over the entire source wavelength range, thereby generating a polarized light beam; and
   to direct and focus the polarized light beam to a target position inside the skin at a predetermined focus depth below an outer surface of the skin such that a direction or orientation of the polarization is the same throughout the entire source wavelength range;
   the measurement system further comprising:
   a first detector configured and arranged to directly detect the first light intensity within a first predetermined detection wavelength range of light reflected from the target position;
   a second detector configured and arranged to directly detect the second light intensity within a second predetermined detection wavelength range of light reflected from the target position; and
   a comparator, coupled to the first detector and the second detector and configured and arranged to directly determine a difference between the first light intensity and the second light intensity based on the directly detected first and second light intensities;
   wherein, with reference to a reflected spectrum of light of the polarized light beam reflected by natural collagen when present at the target position, said reflected spectrum comprising a plurality of adjacent first and second wavelength ranges, wherein in said first wavelength ranges constructive interference prevails between the polarized light beam and the natural collagen, and wherein in said second wavelength ranges destructive interference prevails between the polarized light beam and the natural collagen:
the first detection wavelength range is predetermined and/or controlled to be confined to one or more of said first wavelength ranges; and
the second detection wavelength range is predetermined and/or controlled to be confined to one or more of said second wavelengths ranges.

2. The measurement system according to claim 1, wherein the first detection wavelength range is predetermined and/or controlled to be confined to one or more of said plurality of first wavelength ranges wherein constructive interference of second order or higher order prevails between the polarized light beam and the natural collagen, and wherein the second detection wavelength range is predetermined and/or controlled to be confined to one or more of said plurality of second wavelength ranges wherein destructive interference of second order or higher order prevails between the polarized light beam and the natural collagen.

3. The measurement system according to claim 1, wherein the optical system is configured and arranged to focus the polarized light beam at a target position between 100 microns and 1000 microns below the outer surface of the skin.

4. The measurement system according to claim 1, wherein the second detection wavelength range is predetermined and/or controlled to extend over a band of less than 100 nm.

5. The measurement system according to claim 1, wherein a difference between a central wavelength of the first detection wavelength range and a central wavelength of the second detection wavelength range is less than 300 nm.

6. The measurement system according to claim 1, wherein the optical system is configured and arranged to generate a linearly polarized light beam at the target position in the skin.

7. The measurement system according to claim 1, wherein the first detection wavelength range is predetermined and/or controlled to be confined to a single one of said plurality of first wavelength ranges, and wherein the second detection wavelength range is predetermined and/or controlled to be confined to a single one of said plurality of second wavelengths ranges, wherein said single one of said plurality of first wavelength ranges is adjacent to said single one of said plurality of second wavelength ranges.

8. The measurement system according to claim 1, wherein the first detector comprises:
at least two detector channels, each detector channel being configured and arranged to detect a light intensity within a different one of said plurality of first wavelength ranges; and
a processor, coupled to each detector channel and configured and arranged to determine the first light intensity from the light intensities detected by said at least two detector channels.

9. The measurement system according to claim 1, wherein the second detector comprises:
at least two detector channels, each detector channel being configured and arranged to detect a light intensity within a different one of said plurality of second wavelength ranges; and
a processor, coupled to each detector channel and configured and arranged to determine the second light intensity from the light intensities detected by said at least two detector channels.

10. The measurement system according to claim 7, wherein the first detector comprises a single photodiode to measure the first light intensity, and the second detector comprises a single photodiode to measure the second light intensity.

11. The measurement system according to claim 1, wherein a central wavelength of the source wavelength range is in a range from visible light to infrared light.

12. A skin treatment system for denaturation of collagen, wherein the skin treatment system comprises the measurement system according to claim 1.

13. The measurement system according to claim 1, wherein the second detection wavelength range is predetermined and/or controlled to extend over a band of less than 50 nm.

14. The measurement system according to claim 1, wherein the second detection wavelength range is predetermined and/or controlled to extend over a band of less than 30 nm.

15. The measurement system according to claim 1, wherein the second detection wavelength range is predetermined and/or controlled to extend over a band of less than 20 nm.

16. The measurement system according to claim 1, wherein a difference between a central wavelength of the first detection wavelength range and a central wavelength of the second detection wavelength range is less than 100 nm.

17. The measurement system according to claim 1, wherein a difference between a central wavelength of the first detection wavelength range and a central wavelength of the second detection wavelength range is less than 50 nm.

18. The measurement system according to claim 1, wherein a difference between a central wavelength of the first detection wavelength range and a central wavelength of the second detection wavelength range is less than 30 nm.

19. The measurement system according to claim 1, wherein the comparator is connected to a treatment source to control at least one of a treatment duration or a treatment intensity.

20. The measurement system according to claim 1, the measurement system further comprising means for controlling the polarization direction to allow a user to determine an optimal orientation of the polarization direction.

21. The measurement system according to claim 1,
wherein the first detector comprises two or more detector channels, each detector channel being configured and arranged to detect a light intensity within a different one of the first wavelength ranges of the reflected light wherein constructive interference occurs or prevails,
wherein the second detector comprises two or more detector channels, each detector channel being configured and arranged to detect a light intensity within a different one of the second wavelength ranges of the reflected light wherein constructive interference occurs or prevails.

* * * * *